United States Patent [19]

Gold et al.

[11] Patent Number: 4,950,783

[45] Date of Patent: Aug. 21, 1990

[54] TREATMENT OF HYPERTENSION

[75] Inventors: Elijah H. Gold, West Orange; Wei K. Chang, Livingston, both of N.J.

[73] Assignee: Schering Corporation, Kenilworth, N.J.

[21] Appl. No.: 922,598

[22] Filed: Oct. 24, 1986

Related U.S. Application Data

[63] Continuation of Ser. No. 551,387, Nov. 14, 1983, Pat. No. 4,619,919, which is a continuation-in-part of Ser. No. 137,935, Apr. 7, 1980, abandoned, which is a continuation-in-part of Ser. No. 89,077, Oct. 29, 1979, abandoned, which is a continuation-in-part of Ser. No. 944,516, Sep. 20, 1978, abandoned.

[51] Int. Cl.$^5$ .................. C07C 237/30; A61K 31/615; A61K 31/165
[52] U.S. Cl. .................................... 562/584; 562/585; 562/595; 564/165
[58] Field of Search .................. 564/165; 260/501.17; 514/166, 620, 554, 555; 562/584, 585, 595

[56] References Cited

U.S. PATENT DOCUMENTS

| | | | |
|---|---|---|---|
| 3,732,300 | 5/1973 | Lunts et al. | 260/559 S |
| 4,012,444 | 3/1977 | Lunts et al. | 564/165 |
| 4,173,583 | 11/1979 | Gold et al. | 564/165 X |
| 4,619,919 | 10/1986 | Gold et al. | 514/166 |
| 4,658,060 | 4/1987 | Gold et al. | 564/165 |

FOREIGN PATENT DOCUMENTS

| | | |
|---|---|---|
| 1557677 | 1/1969 | France . |
| 1541932 | 3/1979 | United Kingdom . |
| 1541933 | 3/1979 | United Kingdom . |

OTHER PUBLICATIONS

Maronde et al., *The Amer. J. of Med.*, pp. 40–46, Oct. 17, 1983.
Levy, *Arch. Int. Pharmacodyn. Ther.*, 204, pp. 143–147 (1973).
Bailey, *Br. J. Clin. Pharmacol.*, (1979), pp. 1355–1405.
Simpson et al., *Br. J. Pharmacol.* (1979), 8, 1795–1825.
Famet et al., *Br. J. Pharmac.* (1972), 45, 660–675.
Brittain et al., *Br. J. Pharmac.* (1982), 77, 105–114.
Bragden et al., *Drugs* 15: 251–270 (1978).
Drew et al., Clinical and Experimental Hypertension, 1(5), 597–611 (1979).
Gold et al., *J. Med. Chem.* 1982, 25, 1363–70.
Robson, *J. Pharm. Exp. Therap.*, 175, 157–167 (1970).
Sybertz et al., *J. Pharm. Exp. Therap.*, 218, 435–443 (1981).
Louis et al., *The Lancet*, 452–3, Feb. 25, 1978.
Baum et al., *J. Pharm. Exp. Therap.*, 218, 444–452 (1981).
Brittain, et al., Proceeding of the B.P.S. Dec. 16th–18th, 1980, pp. 282P–283P.
McLean, *Medicinal Chemistry*, 2nd Ed., Edited by Bauger, p. 602, 1960.
Script, p. 20, Apr. 2, 1977.
Levy, Arch. Int. Pharmacodyn. Ther., 204, 143 (1973).
A. M. Barnett, J. Pharm. Pharmacol., 21:241–247 (1969). A Comparison of the Effects of (+)-Propranolol and (+)-Propranolol in Anaesthetized Dogs'; B-Receptor Blocking and Haemodynamic Action.

*Primary Examiner*—Carolyn S. Elmore
*Attorney, Agent, or Firm*—James R. Nelson; Stephen I. Miller

[57] ABSTRACT

Compositions containing (−)-5-{(R)-1-Hydroxy-2[(R)-1-methyl-3-phenylpropyl)amino]ethyl}salicylamide exhibit potent vasodilating β-adrenergic blocking properties and are useful for the treatment of hypertension.

3 Claims, No Drawings

TREATMENT OF HYPERTENSION

This application is a continuation of application Ser. No. 551,387, filed Nov. 14, 1983 (now U.S. Pat. No. 4,619,919), which is a continuation-in-part of application Ser. No. 137,935, filed Apr. 7, 1980 (now abandoned), which in turn is a continuation-in-part of application Ser. No. 089,077, filed Oct. 29, 1979 (now abandoned), which in turn is a continuation-in-part of application Ser. No. 944,516, filed Sept. 20, 1978 (now abandoned).

This invention relates to a novel composition which possesses a potent and unusual profile of antihypertensive activity i.e., that of a vasodilating-β-blocker and to the method of using it for the treatment of hypertension. The active compound of this composition is an optical isomer of one of the diastereomers of the compound labetalol which is described in Lunts, et al, U.S. Pat. No. 4,012,444. Chemically, this isomer is (−)-5-{(R)-1-hydroxy-2-[(R)-1-(1-methyl-3-phenylpropyl)amino]ethyl}salicylamide (hereinafter for convenience referred to as the R,R-enantiomer).

Whereas the foregoing Lunts et al patent recognizes that compounds such as labetalol have optically active forms, no example of an optically active form is given. The subject enantiomer isomer, or indeed any of the optical isomers of labetalol, has heretofore been unknown in the art.

Labetalol has been characterized as a "new kind of antihypertensive" since it has the secondary effect of having β-blocking activity as well as its primary action of blockade of α-adrenoceptors in the peripheral arterioles. Its major side-effect, orthostatic hypotension (postural hypotension), is attributable to its α-blocking activity. Although postural responses to labetalol can be reduced by use of appropriate dosage schedules, compounds with less orthostatic potential would represent an improvement. Other symptoms associated with α-blockade, e.g., flushing, dizziness and failure of ejaculation are also observable, (See, for instance, Script, p. 20, Apr. 2, 1977), and patients with congestive heart failure may lower cardiac output by decreasing venous blood return as a result of alpha blockade. Other observable side-effects are discussed in Bailey, R. R. Br. J. Clin. Pharm. 8, 1355, (1979) Supplement and Simpson, F. O., Br. J. Clin. Pharm. 8, 1795, (1979) Supplement.

The unique pharmacological profile of labetalol and its use as an antihypertensive agent are suggested to be largely a function of the exquisite balance of its α- and β-adrenergic blocking activities. As disclosed in the file history of the aforesaid Lunts et al patent, even slight changes in the chemical structure of labetalol deleteriously affect this ratio, and even in those few variants where the ratio is retained, the absolute potencies of those variants are taught to be too low to be useful as antihypertensive agents. More specifically, the Lunt's file history teaches that the dose-response curves for β-blockade and α-blockade must be close together and preferably overlap to some degree. The optimum β:α-blocking ratio is taught to be in the range of 2 to 10 because a lower ratio would not certainly avoid tachycardia or postural hypotension (orthostasis) and a higher ratio would require the administration of excessively large and possibly toxic doses before the correct degree of α-adrenoceptor blockade was obtained.

We have surprisingly found that the subject R,R-enantiomer exhibits, as compared to labetalol, a totally distinct pharmacological profile. For instance, it possesses a high increase in β-adrenergic blocking potency, yet a decrease in the α-adrenergic blocking potency. The R,R-enantiomer has been shown to be approximately 4 times as potent as labetalol in blocking beta receptors and only ½ as potent in blocking alpha receptors by Sybertz et al, J. Pharmacol. Exp. Ther., 218, 435 (1981). The α- and β-blocking activities may be determined by the methods described in Farmer et al, Brit. J. Pharm., 45, 660 (1972); Robson, J. Pharm. Exp. Therap., 175, 157 (1970); and Levy, Arch. Int. Pharmacodyn. Ther., 204, 143 (1973). Thus, the β:α ratio of the R,R-enantiomer is markedly higher than the ratio of labetalol. See, for instance, Gold et al, Journal of Medicinal Chemistry, 25, 1363 (1982) and Brittain et al, Preceedings of the B.P.S. 282 P, (Dec. 16–18, 1980). These ratio potency changes could not have been predicted on a theoretical basis and they give the R,R-enantiomer a significantly different β/α-blocking ratio from that of the parent labetalol. In fact, the α-blocking activity of the R,R-enantiomer is so low as to be insignificant as noted in Gold et al and Brittain et al supra. Based on the teachings of the Lunt file history, the projected dose required of the R,R-enantiomer for effective blood pressure lowering would be enormous, i.e., several orders of magnitude that of labetalol. At such a dose, toxic side effects would be expected to occur, e.g., direct cardiac depression.

Yet, most surprisingly in view of the teachings of Lunts et al, the R,R-enantiomer possesses potent antihypertensive properties at dosages comparable to labetalol as well as a rapid onset of action. Moreover this is accomplished without significant toxic side effects such as postural hypotension or rise in liver enzymes such as SGOT and SGPT which are evidence of liver dysfunction.

Additionally, because of the lack of significant side effects the R,R-enantiomer can be given in full daily dose only once a day if desired, whereas, in order to obtain the desired antihypertensive effects with labetalol and avoid its side effects, divided doses must be given at least twice a day, to avoid the side effects of a large dosage.

Additionally, we have found that the R,R-enantiomer possesses much increased direct vasodilatory activity over that of labetalol. See Baum et al, J. Pharmacol. Exp. Ther. 218, 444, (1981) wherein it is reported that the R,R-enantiomer is approximately seven times as potent a direct vasodilator as labetalol and this, together with its lower alpha blocking potency would result in an antihypertensive activity with less orthostatic effects or other side effects including those attributable to the fact that alpha blockade affects the peripheral blood vessels. The overall pharmacological profile of the R,R-enantiomer is thus that a vasodilating-β-blocker which is in marked contrast to that of labetalol which is a β-blocker, α-blocker anti-hypertensive. By reducing blood pressure by two independent but complementary mechanisms—β-blockade and vasodilation—the R,R-enantiomer would be more effective than traditional β-blocking antihypertensive agents. It is this much increased direct vasodilating property which enables the R,R-enantiomer to be an effective anti-hypertensive without the side effects caused by α-block effects. The direct vasodilating action results in more blood in the vessels of the muscles rather than the peripheral blood vessels, thus avoiding side effects such as flushing.

One of the two diastereomers of labetalol has been taught to possess antiarrhythmic properties for individuals who have suffered myocardial infarctions (see Belgian Patent No. 840,779 and U.S. Pat. No. 4,173,583). This diastereomer, called A, is identified as the one whose hydrochloride salt has the higher melting point (identified as Isomer 1 in U.S. Pat. No. 4,012,444). The optical isomer R,R of this application is derived from diastereomer B. We have found the R,R-enantiomer to have significantly higher β-blocking activity over that of labetalol and α-blocking activity which is significantly less than that of labetalol as discussed above.

The R,R compound of this invention is physically characterized as having a hydrochloride salt which exists in two crystalline forms, one melting at about 133°–134° C., and the other melting at about 192°–193 5° C. The hydrochloride of the R,R-enantiomer possesses an $[\alpha]_D^{26}$ of about $-30.6°$ (conc. 1% in ethanol). It may be prepared preferably by stereoselective synthesis as described in U.S. patent application Ser. No. 371,622, filed Apr. 26, 1982 which is incorporated herein by reference. The process disclosed therein produces the R,R-enantiomer via reduction of the precursor 2-(O-protected)-5-[(R)-α-methylbenzyl]-N-[(R)-1-methyl-3-phenylpropyl)glycyl]benzamide followed by removal of the protecting groups to yield a mixture consisting mainly of the desired R,R stereoisomer and a very minor amount of its S,R diastereomer. The mixture is readily resolved by salt formation to the desired R,R-compound of this invention.

The R,R-compound can also be prepared by the stereo-selective synthesis depicted in the following reaction Scheme I:

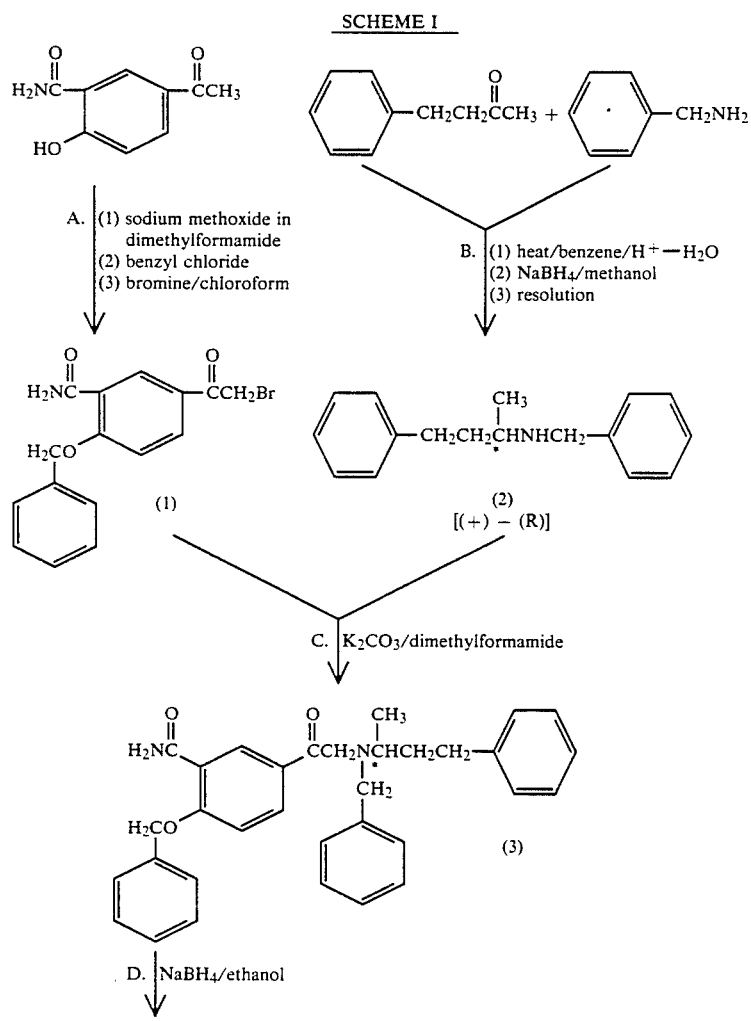

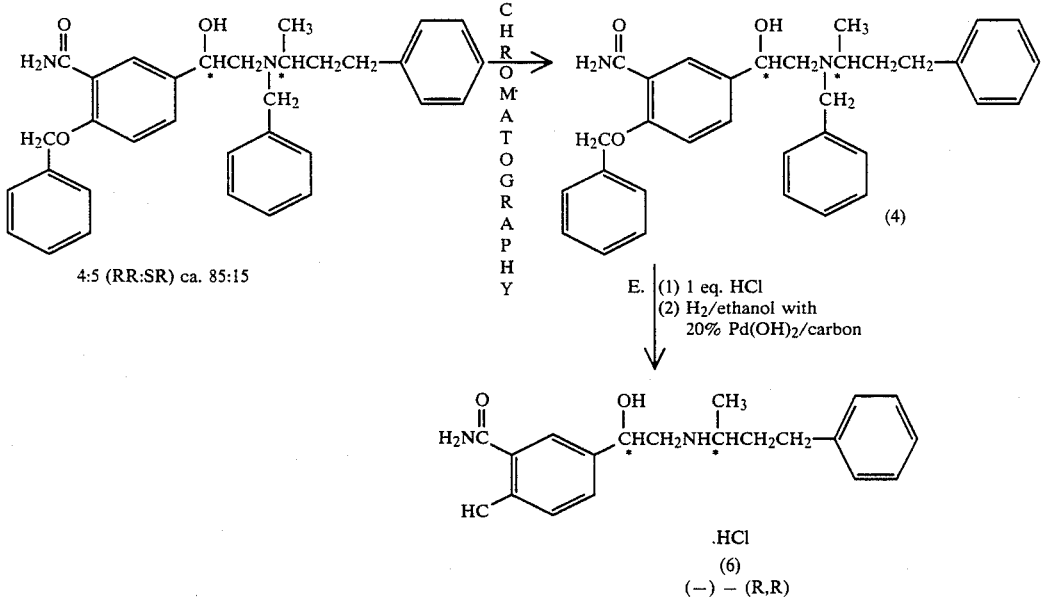

-continued
SCHEME I

4:5 (RR:SR) ca. 85:15

E. (1) 1 eq. HCl
(2) H₂/ethanol with 20% Pd(OH)₂/carbon (6)
(−) − (R,R)

The active compound of this invention, (−)-5-[(R)-1-hydroxy2[(R)-(1-methyl-3-phenylpropyl)amino]ethyl salicylamide can be utilized in the treatment of hypertension in the manner already well known for labetalol, i.e., by oral and parenteral administration, with different specificity of action. Typically, the daily oral dose for humans will be within the range of 100 to 1200 mg and preferably 200 to 800 mg, preferably given once a day, although divided dosages can be given if desired. Thus, it may be formulated with suitable pharmaceutical excipients to provide oral formulations, such as pills, tablets, capsules, powders, or parenteral formulations such as solutions or suspensions. Dosage units preferably contain from 20 to 200 mg and, more preferably, from 50 to 100 mg of the R,R enantiomer or one of its salt forms. Greater predictability of action, less patient-to-patient variability and much less liability for α-adrenergic blockage side effects can be expected than analogous therapy with labetalol. Although, as mentioned above herein, the side effects caused by labetalol can be lessened in most cases by a proper dosage regimen.

Included within the scope of this invention as the active compound are the pharmaceutically acceptable acid addition salts of the R,R-enantiomer. Such salts, which can be prepared by well known techniques, are exemplified by the hydrochloride, sulfate, maleate, tartrate and citrate.

The following examples describe in detail the preparation of the compound and compositions of the present invention. It will be apparent to those skilled in the art that many modifications, both of materials and methods, may be practiced without departing from the purpose and intent of this invention.

EXAMPLE 1

A. Into a Paar hydrogenation bottle charge: 121.2 g (1.00 mole) of D-(+)-α-methylbenzylamine, 173.4 g (1.17 mole, 17% excess) of benzylacetone, 60.1 g (1.00 mole) of glacial acetic acid and 600 ml isopropanol. Add 80 g (wet weight) of Raney Nickel (Grace No. 28), washed with water to neutral and then with isopropanol to remove the water. Hydrogenate the mixture under 60 psi hydrogen pressure.

Filter the resulting mixture through a short bed of celite. Wash the catalyst and celite with 3×100 ml of isopropanol. Combine the isopropanol solutions and dilute with a further 660 ml of isopropanol. To this solution add, with efficient stirring over a period of about 30 minutes, 467 ml of a 2.25N (1.05 mole) solution of gas HCl in isopropanol. After about half of the HCl/isopropanol is added, the product starts precipitating. The temperature rises to 33° C. Cool to ambient temperature and stir for 3 hours. Filter the solid and wash on filter with 100 ml isopropanol. Dry the resulting solid at 50° C. to yield a white solid m.p. 216.5°–218° C., $[\alpha]_D^{26} = +59.6°$ (1% in MeOH).

Recrystallize the solid from isopropanol using 15 ml of solvent per gram of material. Cool to ambient temperature and stir for 3 hours. Filter and wash the solid on the filter with 2×100 ml isopropanol. Dry the solid at 50° C. to constant weight to obtain a white crystalline solid, m.p. 219°–220.5° C., $[\alpha]_D^{26} = +60.8°$ (1% in MeOH).

B. Charge 78.0 g (0.269 mole) of the R,R-amine-HCl salt, 390 ml toluene and 135 ml of a 3 molar aq. NaOH solution (0.405 mole, 50% excess) into a vessel and heat at 80° C. with stirring, under nitrogen for 1 hour. Separate the resulting layers. Extract the water layer with 80 ml toluene. Combine toluene extracts and wash with 2×80 ml saturated aq. NaHCO₃ (pH of last washing should be 9), with 2×80 ml water (last washing should be neutral) and 80 ml saturated aq. NaCl. Dry the toluene extracts with Na₂SO₄. Remove the solvent in vacuo. Distill the product at 128°–134°/0.9 mm Hg. A clear colorless liquid, 67.3 g (98.7% yield), $[\alpha]_D = +78.4°$ (neat) or $[\alpha]_D = +115.2°$ (10% in MeOH) is obtained.

C. In a 1 liter three necked flask equipped with stirrer, thermometer and reflux condenser charge 200 ml of dimethylformamide (dried over 4A molecular sieves), 83.6 g (0.24 moles) of 2-(phenylmethoxy)-5-(bromomethylcarbonyl)benzamide, 50.7 g (0.2 moles) of the amine from Step 8 and 35 ml (29 g; 0.5 moles) of propylene oxide.

Heat the stirred suspension to 45°–47° C. and maintain the resulting solution at this temperature for 24 hours. The color or the solution changes from yellow to orange and later to reddish orange. Protect the reaction mixture from light at all times during the reaction and the subsequent work-up.

After 24 hours remove a sample and check the completion of the reaction. When the reaction is complete, cool the reaction mixture to room temperature and pour into a stirred mixture of 600 ml of water and 200 ml of $CH_2Cl_2$.

Separate the phases, extract the aqueous layer twice with 200 and 100 ml of $CH_2Cl_2$ and wash the combined organic layers with 3×200 ml of water. Dry thoroughly over anhydrous $Na_2SO_4$ or $MgSO_4$, filter, wash the cake with 2×50 ml of $CH_2Cl_2$ and remove the solvent under reduced pressure (120 mm Hg and water bath temperature of about 40° C.).

Dissolve the red, viscous residue in 500 ml of 2B ethanol and proceed immediately to the next step.

D. Cool the solution of amino-ketone obtained from Step C to 5° C.+2° C. under a blanket of nitrogen in a 2 liter three necked flask equipped with a mechanical stirrer and thermometer.

Add to the reaction mixture 7.6 g (0.2 moles) of $NaBH_4$ in portions such as to maintain the temperature and to avoid violent frothing of evolving $H_2$. After the addition is complete, maintain the reaction mixture at 5° C.+2° C. for an hour then let slowly warm to room temperature and continue to stir the mixture for 16–18 hours. Provide intermittent cooling to avoid temperatures higher than 25° C.

Check for completion of reduction by the absence of starting amino-ketone. After completion of the reaction, distill out about 350 ml of EtOH under reduced pressure—approximately 120 mm Hg—and up to a pot temperature of 40° C.

Add 500 ml of water and reflux the mixture for 1 hour (pot temperature about 86° C.), after which, distill off about 150 ml of EtOH at atmospheric pressure. Cool the reaction mixture to 40° C. and extract the yellow, soft resin that separates with 300 ml of $CH_2Cl_2$. Cool the two phase mixture to room temperature, separate and extract the aqueous layer with 125 ml of $CH_2Cl_2$. Wash the combined organic layers with 2×200 ml of water. Dry the solution over anhydrous $Na_2SO_4$ or $MgSO_4$, filter and wash the cake with 2×50 ml of $CH_2Cl_2$.

Remove solvent under reduced pressure. Dissolve the residue in 650 ml of EtOH. Add 12 g (11.5 ml, 0.2 moles) of acetic acid and 6.25 g of Darco G-60 (activated carbon, Atlas Powder Co., Wilmington, Del.) heat to 65° C. and stir for 10 minutes at 65° C. Filter hot through a celite bed, and wash the resulting cake with 3×150 ml of hot ethanol; the resulting ethanol solution being used in Step 5.

E. Charge the ethanolic solution obtained in Step D into a hydrogenation flask, cool the contents in an ice-bath and add, under a blanket of $N_2$ 10 g of 5% Pd/C. Allow the solution to warm to room temperature and reduce in a Parr apparatus with $H_2$ under about 60 psi pressure.

After the reduction is complete, filter the catalyst through a celite bed and wash the cake with 2×125 ml of ethanol.

Add to the filtrate a solution of 75.28 g (0.2 moles) of dibenzoyl-d-tartaric acid monohydrate in 200 ml of ethanol. Seed with good quality salt and stir the mixture at room temperature for 3 days. A fine white precipitate slowly forms.

Filter the precipitated salt, wash with 125 ml of ice-cold ethanol and dry in a draft oven at 50° C. A white powder is obtained (m.p. 168°–170° C. to 173.5°–175° C., uncorrected).

Recrystallize the crude salt from 1400 ml of boiling 90% aqueous ethanol. After dissolution is complete, cool to room temperature, seed with the desired R,R DB-d-TA salt and stir the resulting suspension for 16–18 hours. Filter the precipitate, wash with 2×100 ml of 90% aqueous and dry in a draft oven at 50° C. 71.5–73 g of purified salt is obtained (m.p. 175°–176° C., uncorrected).

F. Into a three-neck round bottom flask equipped with a mechanical stirrer, thermometer, addition funnel and nitrogen bubbler charge: 6.87 g (0.01 mole) of pulverized DB-d-TA salt of the R,R stereoisomer obtained from Step E and 103 ml of isopropanol. Stir the mixture for about 30–45 minutes until a paste like, but very fluid and easily stirrable mixture is obtained. Add, in a fast stream, 4.8 ml of a 2.19N solution of HCl gas in ethanol (0.0105 mole; 5% excess). Stir the mixture efficiently, at ambient temperature, for about 6 hours. Filter the solid and wash on a filter with 3×12.5 ml of isopropanol. Dry in draft oven at 50° C. to constant weight to obtain the HCl salt of the R,R stereoisomer as a colorless solid, 3.43–3.46 g, m.p. 192°–193° C., rotation $\alpha = -15.3°$; $-15°$ ($D_MF$, C=1) diastereomeric purity: 98.9%, >99°.

EXAMPLE 2

A. 4-Benzyloxy-α-bromo-3-carboxamidoacetophenone (1)

To a solution of 115.4 g (0.644 mol) of 5-acetyl-salicylamide in 1.2 liter of dimethylformamide add 33.1 g (0.613 mol) of sodium methoxide in small portions, with cooling and stirring. Heat the mixture on a steam bath and add 75 ml (0.652 mol) of benzylchloride dropwise. Continue heating and stirring for 7 hours. After stirring and cooling, pour the mixture into 6 liters of ice-water containing 15 g of $Na_2CO_3$. Filter, wash well with water, digest with 700 ml of ethanol, chill and refilter to obtain analytically pure 4-benzyloxy-3-carboxamidoacetophenone, m.p. 157°–160° C. To a refluxing, stirred solution of 127.0 g (0.47 mol) of 4-benzyloxy-3-carboxamidoacetophenone in 1.2 liter of chloroform, add a few ml of $Br_2/CHCl_3$ solution [76.5 g (0.49 mol) bromine 220 ml chloroform] until the color is discharged (ca. 5–10 min.). Cool the solution to room temperature, and with stirring at room temperature, add the remaining $Br_2/CHCl_3$ solution dropwise until precipitation begins, after which, reflux the reaction mixture and continue the dropwise addition. After refluxing for 10 min. following completion of the addition, chill the solution in an ice bath, filter and then wash with cold chloroform. Stir the crude solid for 20 min. in 800 ml of ice-cold water, filter, wash well with water and dry. Recrystallize from methylethyl ketone to afford two crops of the product (1), m.p. 150°–152° C. and m.p. 146°–149° C. both of which are usable for the preparation of 2-O-benzyl-5-[N-benzyl-N-((R)-1-methyl-3-phenylpropyl)glycyl]salicylamide (3).

B. (R)-(+)-N-Benzyl-1-methyl-3-phenylpropylamine (2)

In an apparatus fitted with a Dean Stark trap, reflux a solution of 1.0 kg (6.75 mol) of benzylacetone, 725 g (6.75 mol) of benzylamine and 5.0 g of α-toluenesulfonic acid hydrate in 7 liters of benzene for 14 hours. Remove the solvent in vacuo, and dissolve the residue in 6.5 liters of methanol. With cooling and stirring, carefully add 125 g of NaBH$_4$ and stir the mixture for 16 hours at room temperature. Remove the methanol in vacuo, and add 2 liters water and 4 liters benzene, and extract the product into the benzene. After drying (MgSO$_4$), filter and distill (b.p. 145°–150° C./0.5 mm). Dissolve 1,028 g (4.288 mol) of the distillate and 1.23 kg (4.328 mol) of N-α-toluenesulfonyl-(L)-leucine in 7.2 liters of boiling ethanol and allow to cool to room temperature without agitation. Wash the precipitate with a small amount of ice-cold ethanol, recrystallize from 4.8 liters of ethanol, wash with ice-cold ethanol and filter off the solid product that is highly enriched with the salt of the undesired S enantiomer. Combine the mother liquor from the original precipitation and that from the recrystallization, remove the solvent and recover the free base by basifying with 500 ml of 20% aqueous NaOH and extracting with benzene. After drying (MgSO$_4$), filtering and removing the benzene, dissolve the residue [487 g (2.04 mol)] and 346 g (2.06 mol) of N-acetyl-(L)-leucine in 2.0 liters of boiling ethanol and allow the solution to cool to room temperature. Filter and recrystallize once from 1.8 liter of ethanol followed by recrystallization from 4.0 liters of acetonitrile to obtain the desired R salt, m.p. 151°–152° C. Basify with 400 ml of aqueous 2.5N NaOH, extract with ether, dry (MgSO$_4$), filter and remove the solvent in vacuo to obtain the product (2), $[\alpha]_D^{26} = +4.5°$ (c=5.0, ethanol).

C.
2-O-Benzyl-5-[N-benzyl-N((R)-1-methyl-3-phenylpropyl)glycyl]salicylamide (3)

Stir a mixture of 224 g (0.94 mol) of (R)-(+)-N-benzyl-1-methyl-3-phenylpropylamine, 372 g (ca., 1.07 mol) of 4-benzyloxy-bromo-3-carboxamidoacetophenone and 372 g (2.7 mol) of K$_2$CO$_3$ in 1.6 liters dimethylformamide at room temperature for 4 hours (reaction mildly exothermic). Add 8.7 liters water and extract with ether, dry (Na$_2$SO$_4$), filter, and remove the ether in vacuo (30°–40° C.) to yield the crude product (3) as a syrup.

D. 2-O-benzyl-5{(R)-1-hydroxy-2-[(R)-(1-methyl-3-phenylpropyl)benzylamino]ethyl}salicylamide (4)

Dissolve 520 g (0.94 mol-maximum) of crude 2-O-benzyl-5-[N-benzyl-N-((R)-1-methyl-3-phenylpropyl)-glycyl]salicylamide in 3.1 liters ethanol and, with stirring and cooling, add portionwise 35.5 g (0.94 mol) of NaBH$_4$. Stir the mixture at room temperature for 16 hours, remove the solvent in vacuo, add 3.2 liters water and heat the mixture for 30 min. on a steam bath. Cool, extract with benzene, dry (MgSO$_4$), filter, and remove the solvent in vacuo, and obtain the crude product as a syrup (ratio R,R:S,R ca. 85:15). Chromatograph 47 g of the crude mixture on 1.5 kg of thin layer grade silica gel with 3:1 CHCl$_3$:EtOAc and obtain the pure product (4), which is eluted first.

E.
(−)-5-{(R)-1-Hydroxy-2-[(R)-(1-methyl-3-pheylpropyl)amino]ethyl}salicylamide hydrochloride salt (6)

1. Treat a solution of 3.0 g. (0.0059 mol.) of 2-O-benzyl-5-(R)-1-hydroxy-2-[(R)-(1-methyl-3-phenylpropyl)-benzylamino]ethyl }salicylamide in 30 ml of ethyl ether with 2N ethereal hydrogen chloride until no further precipitation occurs. Wash the precipitate, 2-O-benzyl-5- (R)-1-hydroxy-2-(R)-(1-methyl-3-phenylpropyl)ben-zylamino]ethyl salicylamide hydrochloride, with ether to remove the excess HCl, and dissolve in 100 ml ethanol. To the ethanol solution add 300 mg of a 20% palladium hydroxide on carbon catalyst and hydrogen (3 atm.) in a Paar apparatus with shaking at room temperature for 3 hours. Filter off the catalyst, evaporate, and triturate the solid remaining with isopropanol. Dissolve the solid in 11 ml of 1N NaOH and adjust the pH to about 8 by bubbling in carbon dioxide. Collect the free base that precipitates, wash with water, and dry in vacuo at 40° C. Chromatograph the free base on 450 g of silica gel, and dissolve the pure (tlc) product in 20 ml of boiling acetonitrile. Cool the solution and carefully acidify with 2N ethereal HCl to about pH 2. Solidify the gum which precipitates by refluxing the mixture for 10 minutes. Filter the solid, wash with ethyl ether, and obtain analytically pure product (6), m.p. 192°–193.5° C. (dec.), $[\alpha]_D^{26} = -30.6°$ (c=1.0, ethanol) in a yield of about 66%.

2. Alternatively, hydrogenate a solution of 3.0 g (0.0059 mol) of 2-O-benzyl-5-{(R)-1-hydroxy-2-[(R)-(1-methyl-3-phenylpropyl)benzylamino]ethyl}salicylamide in 150 ml ethanol, containing 5.85 ml of 1N aqueous HCl (0.00585 mmol) and 0.25 g of 20% Pd(OH)$_2$ on carbon, with hydrogen (3 atm) in a Paar apparatus with shaking at room temperature for 3 hours. After filtering off the catalyst, evaporate, digest the residue in boiling acetonitrile, filter, and recrystallize from ethanol to obtain analytically pure product (6), m.p. 192°–193.5° C., dec., $[\alpha]_D^{26} = -30.6°$ (c =1.0, ethanol).

PHARMACEUTICAL FORMULATIONS

In the following examples, the active ingredient is preferably (−)-5-{(R)-1-hydroxy-2-[(R)-(1-methyl-3-phenylpropyl)amino]ethyl }salicylamide hydrochloride, but an equivalent quantity of the (R,R) isomer itself or of another pharmaceutically acceptable acid addition salt, especially a salt named herein, may be substituted:

EXAMPLE 3

| Injectable Solution: | mg./ml. | mg./20 ml. |
| --- | --- | --- |
| Active ingredient | 5.00 | 100.00 |
| Methyl p-hydroxybenzoate | 0.80 | 16.0 |
| Propyl p-hydroxybenzoate | 0.10 | 2.0 |
| Disodium Edetate | 0.10 | 2.0 |
| Citric Acid Monohydrate | 0.08 | 1.6 |
| Dextrose | 40.00 | 800.0 |
| Water for injection qs ad | 1.00 ml. | 20.00 ml. |

Dissolve the p-hydroxybenzoates in a portion of water for injection at 60°–70° C., and cool the solution to 25°–35° C. Charge and dissolve all other excipients and the active ingredient. Bring the solution to final volume, filter it through a sterilizing membrane and fill into sterile containers.

EXAMPLE 4

| Oral Formulations: (a) Capsules: | | |
| --- | --- | --- |
| | Quantities per Tablet | |
| Formula | (mg.) | (mg.) |
| Active ingredient | 50.00 | 100.0 |

-continued

Oral Formulations:
(a) Capsules:

| Formula | Quantities per Tablet (mg.) | (mg.) |
| --- | --- | --- |
| Lactose | 55.75 | 111.5 |
| Corn Starch | 18.75 | 37.5 |
| Magnesium Stearate | 0.50 | 1.0 |
| | 125.00 | 250.0 |

Blend the active ingredient, lactose and corn starch until uniform; then blend the magnesium stearate into the resulting powder. Encapsulate the mixture into suitably sized two-piece hard gelatin capsules.

(b) Tablets

| Formula | Quantities per Tablet (mg.) | (mg.) |
| --- | --- | --- |
| Active ingredient | 50.0 | 100.0 |
| Lactose | 52.75 | 105.5 |
| Corn Starch | 3.0 | 6.0 |
| Water (per thousand tablets) | (30 ml.)* | (60 ml.)* |
| Corn Starch | 18.75 | 37.5 |
| Magnesium Stearate | 0.5 | 1.0 |
| | 125.0 | 250.0 |

*(The water evaporates during manufacture.)

Blend the active ingredient with the lactose until uniform. Blend the smaller quantity of corn starch with the water and add the resulting corn starch paste, then mix until a uniform wet mass is formed. Add the remaining corn starch to the resulting wet mass and mix until uniform granules are obtained. Screen the granules through a suitable milling machine, using a ¾" stainless steel screen. Dry the milled granules in a suitable drying oven until the desired moisture content is obtained. Mill the dried granules through a suitable milling machine using 16 mesh stainless steel screen. Blend in the magnesium stearate and compress the resulting mixture into tablets of desired shape, thickness, hardness and disintegration.

What is claimed:

1. The chemical compound (−)-5-[(R)-1-hydroxy-2-[(R)-1-methyl-3-phenylpropyl)amino]ethyl]salicylamide or a pharmaceutically acceptable salt thereof, substantially free from its other optical isomers.

2. The compound of claim 1 in the form of the hydrochloride salt.

3. The compound of claim 1 in the form of the sulfate, maleate, tartrate or citrate salt.

* * * * *